United States Patent
Wengreen et al.

(10) Patent No.: US 8,306,633 B2
(45) Date of Patent: Nov. 6, 2012

(54) LEAD SYSTEM HAVING A NON-STATIONARY TO STATIONARY ELECTRICAL INTERCONNECT AND METHOD THEREFOR

(75) Inventors: Eric John Wengreen, Blaine, MN (US); Eric Falbe Hammill, Ham Lake, MN (US); Luke Thomas Babler, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 957 days.

(21) Appl. No.: 11/427,177

(22) Filed: Jun. 28, 2006

(65) Prior Publication Data

US 2008/0004683 A1 Jan. 3, 2008

(51) Int. Cl.
*A61N 1/08* (2006.01)
*A61N 1/18* (2006.01)

(52) U.S. Cl. ........ 607/126; 607/127; 607/128; 607/130; 607/131; 607/37

(58) Field of Classification Search .......... 607/126–131, 607/37
See application file for complete search history.

(56) References Cited

U.S. PATENT DOCUMENTS

| | | | | |
|---|---|---|---|---|
| 4,679,572 A * | 7/1987 | Baker, Jr. | ...... | 607/127 |
| 4,966,564 A * | 10/1990 | Foote | ...... | 439/840 |
| 5,020,545 A * | 6/1991 | Soukup | ...... | 607/127 |
| 5,259,394 A * | 11/1993 | Bens | ...... | 607/127 |
| 5,324,325 A * | 6/1994 | Moaddeb | ...... | 607/120 |
| 5,575,814 A * | 11/1996 | Giele et al. | ...... | 607/127 |
| 6,023,638 A * | 2/2000 | Swanson | ...... | 600/510 |
| 6,687,550 B1 * | 2/2004 | Doan | ...... | 607/127 |
| 6,704,605 B2 * | 3/2004 | Soltis et al. | ...... | 607/127 |
| 6,944,489 B2 | 9/2005 | Zeijlemaker et al. | | |
| 7,532,939 B2 * | 5/2009 | Sommer et al. | ...... | 607/127 |
| 2005/0070972 A1 * | 3/2005 | Wahlstrand et al. | ...... | 607/48 |
| 2007/0038280 A1 * | 2/2007 | Bodner et al. | ...... | 607/128 |
| 2008/0288040 A1 * | 11/2008 | Eckerdal et al. | ...... | 607/127 |

* cited by examiner

*Primary Examiner* — Carl H Layno
*Assistant Examiner* — Natasha Patel
(74) *Attorney, Agent, or Firm* — Faegre Baker Daniels LLP

(57) ABSTRACT

A lead system has an elongate body, an active fixation assembly movable relative to the elongate lead body, including a non-stationary electrode. The lead system further includes a non-stationary electrode member and an electrical interconnect electrically connected between the non-stationary electrode member and the stationary electrode member. The electrical interconnect provides a reliable electrical interconnection between the stationary electrode and the non-stationary electrode, while allowing the non-stationary electrode to move relative to the stationary electrode.

19 Claims, 6 Drawing Sheets

LEAD SYSTEM HAVING A NON-STATIONARY TO STATIONARY ELECTRICAL INTERCONNECT AND METHOD THEREFOR

TECHNICAL FIELD

Leads for conducting electrical signals to and from the heart, and more particularly, leads having a rotary to stationary electrical contact.

TECHNICAL BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

To implant the lead within the patient, the lead is often fed intravenously toward the heart. The lead may be implanted within or travel through complex or tortuous vasculature. Once positioned at a desirable location, the lead is fixated to the patient at a location, for example, by actively fixating the lead to the heart. To actively fixate a lead, an element, such as a helical tip at the distal end of the lead, is rotated out of the lead and in to the patient. The helical tip is electrically connected with one or more conductors wound in a coaxial or co-radial configuration. However, co-radial construction does not permit active fixation.

Accordingly, there is a need for a lead with a non-stationary to stationary electrical interconnect.

SUMMARY

A lead system has an elongate body, an active fixation assembly movable relative to the elongate lead body, including a non-stationary electrode. The lead system further includes a non-stationary electrode member and an electrical interconnect electrically connected between the non-stationary electrode member and the stationary electrode member. The electrical interconnect provides a reliable electrical interconnection between the stationary electrode and the non-stationary electrode, while allowing the non-stationary electrode to move relative to the stationary electrode.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
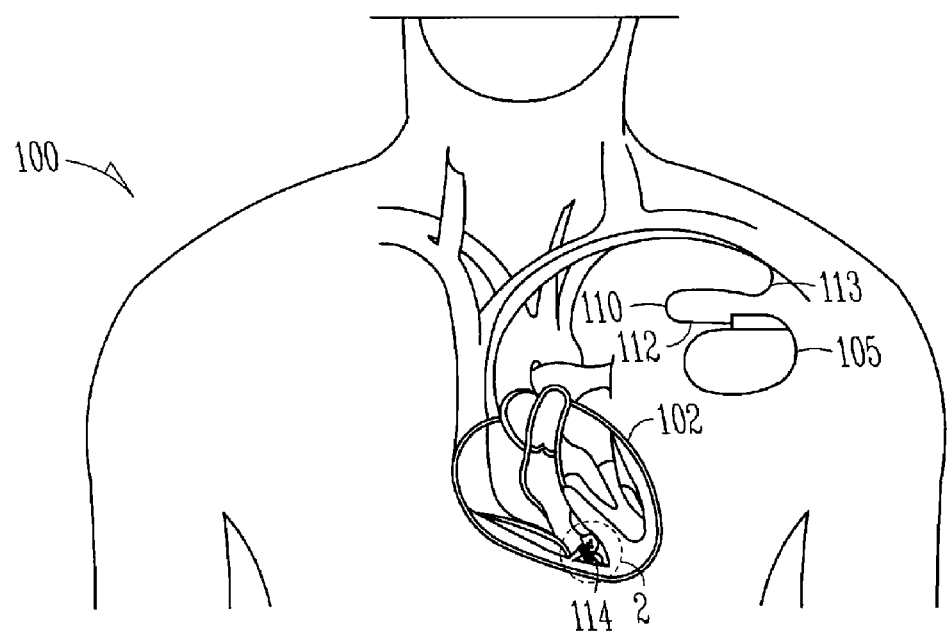
FIG. 1 illustrates a lead system constructed in accordance with at least one embodiment.

An extendable and retractable lead 110 and lead system 100 are illustrated in FIG. 1, that shows a system for delivering and/or receiving electrical pulses or signals to stimulate and/or sense tissue, such as the heart 102. The system 100 includes a pulse generator 105 and a lead 110. The pulse generator 105 includes a source of energy as well as an electronic circuitry portion. The pulse generator 105, in one option, is a battery-powered device that generates a series of timed electrical discharges or pulses. The pulse generator 105 is generally implanted into a subcutaneous pocket made in the wall of the chest. Alternatively, the pulse generator 105 is placed in other places within or near a body, for example, within a subcutaneous pocket made in the abdomen, or in other locations.

Figure 2:
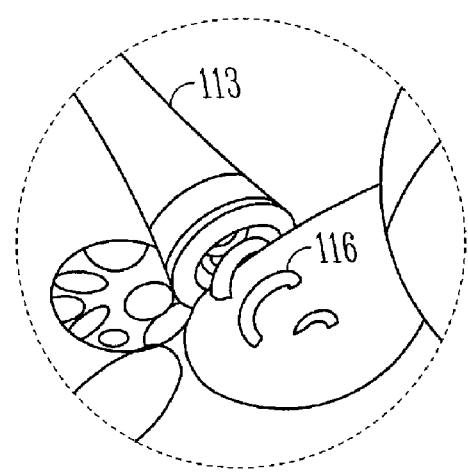
FIG. 2 illustrates a portion of a lead system implanted within tissue constructed in accordance with at least one embodiment.

The lead 110 includes a lead body 113 that extends from a proximal end portion 112, where it is coupled with the pulse generator 105, to a distal end portion 114. The lead 110 further includes at least one non-stationary electrode member 116 (FIG. 2) which electrically couples the lead 110 with tissue, such as the heart 102. The at least one non-stationary electrode member 116 is movable relative to the lead body 113. For example, the non-stationary electrode member 116 is rotatable and/or longitudinally movable relative to the lead body 113. At least one electrical conductor 118 (FIGS. 3A and 3B) is disposed within the lead 110 and extends, in one option, from the proximal end portion 112 to the distal end portion 114 of the lead 110. At least one electrical conductor 118 (FIGS. 3A and 3B) electrically couples the non-stationary electrode member 116 with the proximal end portion 112 of the lead 110. The electrical conductors carry electrical current and pulses between the pulse generator 105 and the non-stationary electrode member 116 (FIG. 2).

Figure 3A:
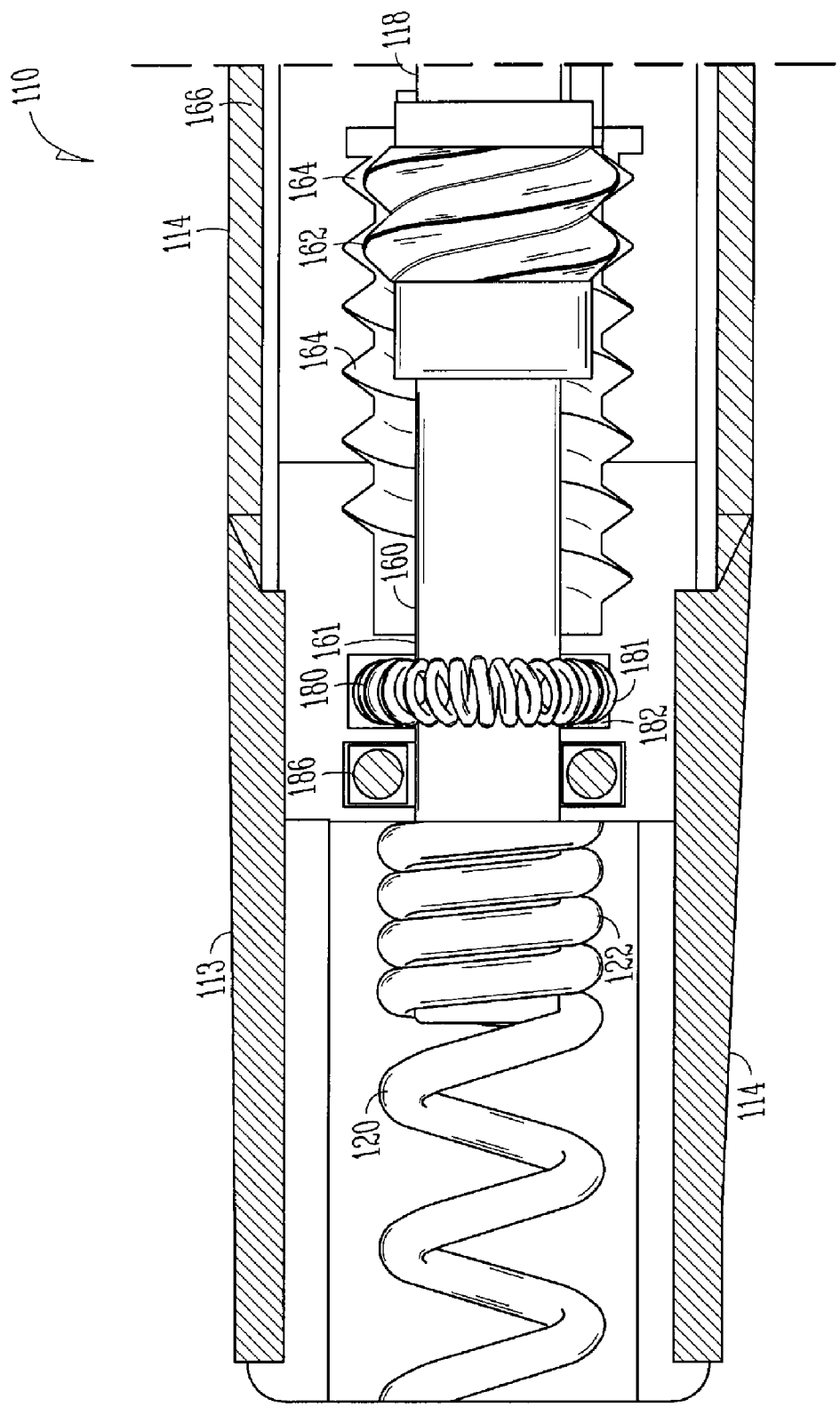
FIG. 3A is a cross-sectional view of a portion of a lead in a retracted position, constructed in accordance with at least one embodiment.
Figure 3B:
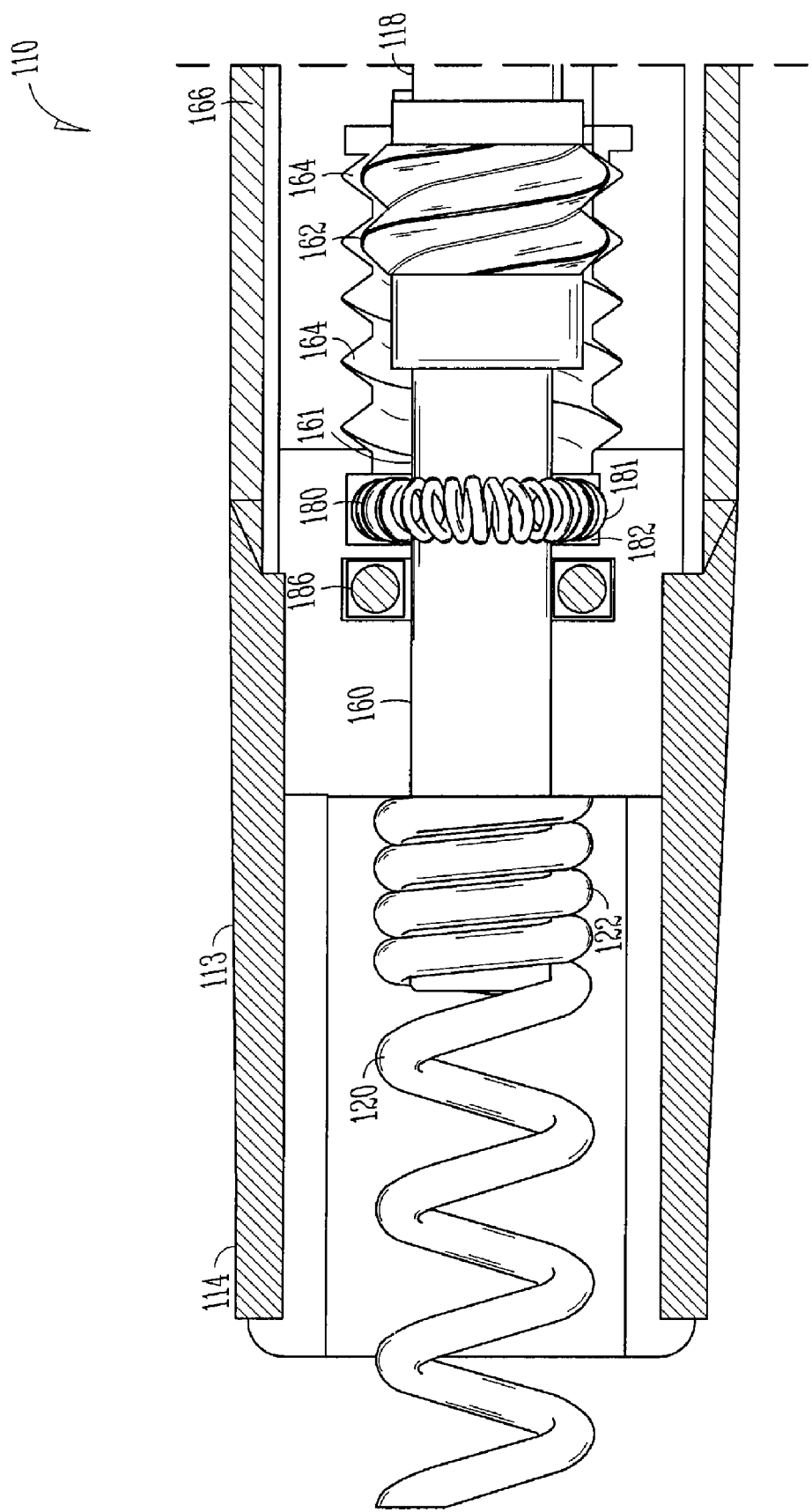
FIG. 3B is a cross-sectional view of a portion of a lead in an extended position, constructed in accordance with at least one embodiment.

FIGS. 3A and 3B illustrate examples for the distal end portion 114 of the lead 110 in greater detail, where FIG. 3A illustrates non-stationary electrode member 116 in a retracted position and FIG. 3B illustrates the non-stationary electrode member 116 in an extended position. The distal end portion 114 includes an active fixation assembly 122 that moves relative to the lead body, where the fixation assembly includes an active fixation member, such as a fixation helix 120. While a fixation helix is illustrated, other active fixation members can be included as well, such as, but not limited to barbs, or sharpened members.

The active fixation assembly 122 and/or the non-stationary electrode member further include an electrode base 160, which a serves as a piston. The piston, in an option, is electrically conductive, and is electrically coupled with the fixation helix 120. The piston is further mechanically coupled with the fixation helix 120, and allows for the fixation helix 120 to be advanced longitudinally through the lead body 113. With movement of the piston, the fixation helix 120 can be moved longitudinally from a retracted position, as shown in FIG. 3A, to an advanced position, as shown in FIG. 3B. When placed in the advanced position, the lead 110 can be fixated with tissue, for example as illustrated in FIG. 2. The fixation helix 120 can also be moved longitudinally from the advanced position to the retracted position as the piston is moved longitudinally.

The piston further includes features that allow it to be moved longitudinally. For example, the piston includes a threaded portion 162 that engages with an internally threaded portion 164 of the housing 166, as shown in FIGS. 3A and 3B. To move the piston in longitudinal movement, the piston is rotated and the threaded portions engage each other to advance the piston and the fixation helix. In an option, the piston is controlled at the proximal portion of the lead 110 (FIG. 1), for example by turning the pin.

The piston is electrically coupled with an electrical interconnect 180 that is included with the lead 110, for example at a distal tip of the lead body 113 (FIG. 1). The electrical interconnect 180 is electrically associated with the piston or the electrode base 160. For example, the electrical interconnect 180 has an inner portion that at least partially surrounds an outer periphery 161 of the piston or electrode base, and optionally is in direct, electrical contact with the piston or the electrode base. In another option, a seal 186 is sealingly engaged with the outer periphery 161 of the piston or electrode base, which assists in preventing harmful fluids from entering the lead 110.

Figure 4:
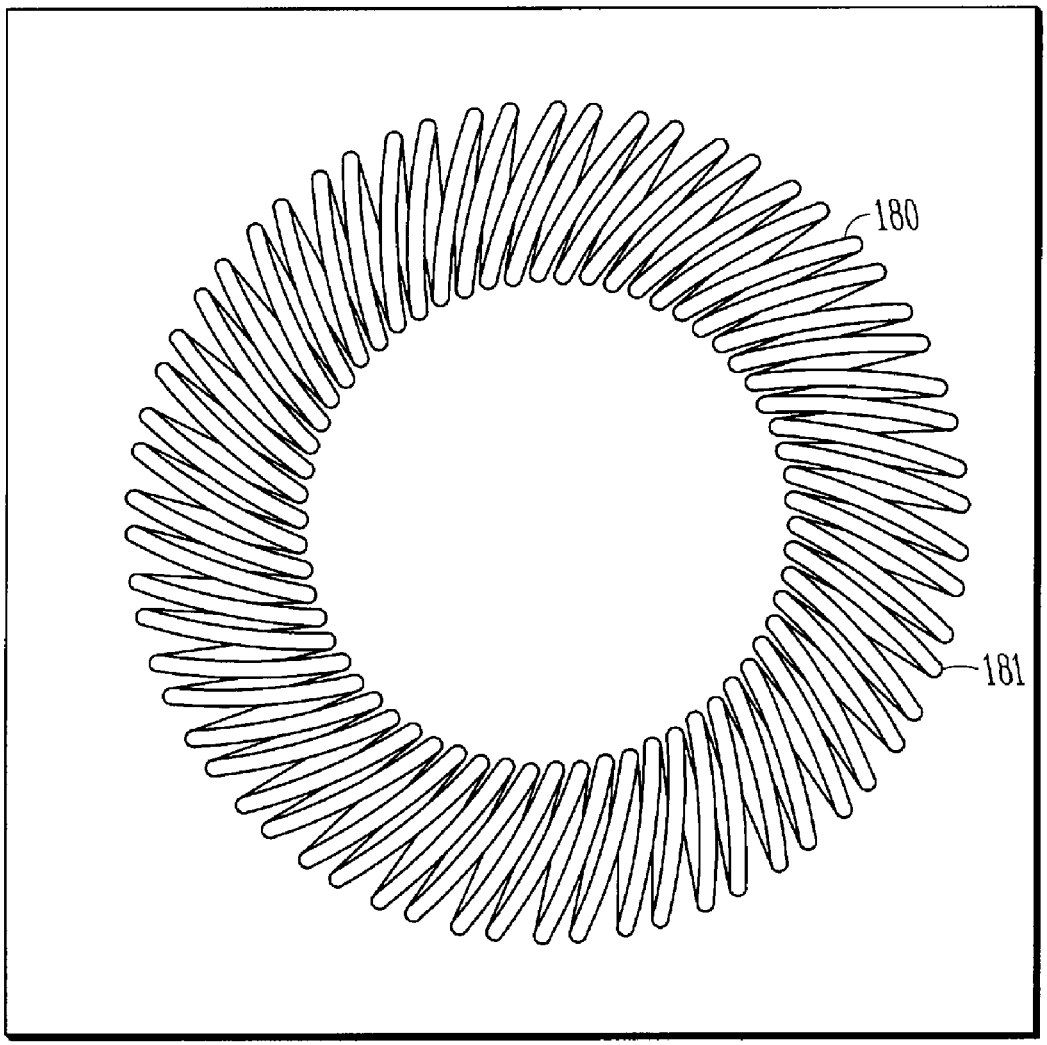
FIG. 4 illustrates an electrical interconnect constructed in accordance with at least one embodiment.

Referring again to the electrical interconnect 180, an example electrical interconnect 180 is illustrated in greater detail in FIGS. 3A, 3B, and 4. In an option, the electrical interconnect 180 is retained by a retention member, such as, but not limited to, a recess 182 or a protrusion coupled with or integral with a stationary electrode member 117, where the stationary electrode member 117 is stationary relative to the lead body 113. In an option, the recess is sized to electrically couple the electrical interconnect 180 with the stationary electrode member 117, for example, by direct contact between an electrically conductive electrical interconnect 180, for example formed of metal, and an electrically conductive stationary electrode member 117.

The electrical interconnect 180 provides a reliable electrical interconnection between the stationary electrode 117 and the non-stationary electrode 116, while allowing the non-stationary electrode to move relative to the stationary electrode 117, for example, as the piston is moved to advance the fixation helix 120. Suitable examples of the electrical interconnect 180 include any member that provides a substantially reliable electrical interconnection between the stationary electrode 117 and the non-stationary electrode that allows for the non-stationary electrode to move relative to the lead body 113 and/or the stationary electrode 117. Further examples include, but are not limited to an annular electrically conductive ring, or a canted coil. An example electrical interconnect 180 is illustrated in FIG. 4, which shows a canted coil 181. The metal canted coil 181 provides the ability to electrically interconnect the stationary electrode with the non-stationary electrode, and can be used regardless of tolerance stack up of the lead assembly, and does not affect the ability of the non-stationary to move. The parameters of the canted coil can be modified, or predetermined to deliver a certain amount of redundant electrical interconnection. The parameters of the canted coil include, but are not limited to, wire diameter, wire material, overall inner diameter, overall outer diameter, number of coils, or number of contact points.

Figure 5:
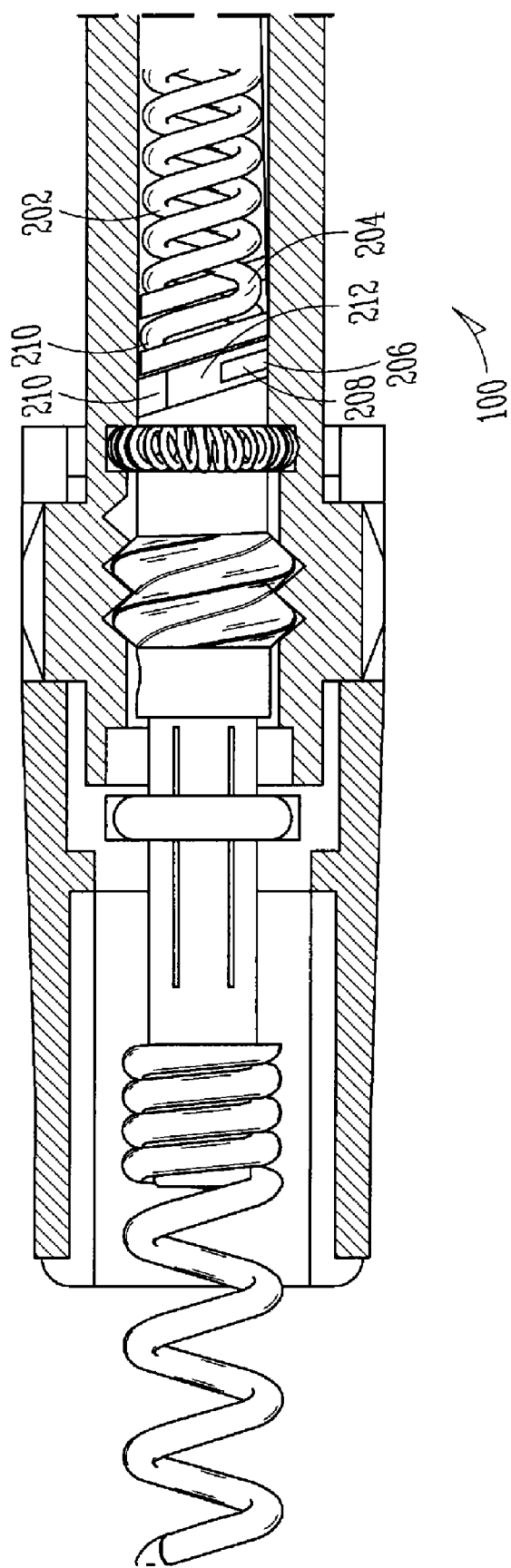
FIG. 5 is a cross-sectional view of a portion of a lead in a constructed in accordance with at least one embodiment.

FIG. 5 illustrates an example of the lead system 100 that includes an electrical connection between a rotating member to a stationary member. The lead system includes a cathodal coil 202 that is co-radially wound with an anoidal coil 204. The cathodal coil 202 is optionally insulated and the anoidal coil 204 is also optionally insulated, where the cathodal coil 202 is insulated from the anoidal coil 204, and they are able to be co-radially wound together.

The lead further includes a break out portion 212 for the anoidal coil 204. A portion 206 of the anoidal coil 204 is stripped, for example, at a proximal end 208. The stripped portion 206 is electrically and optionally mechanically, coupled with the break out portion 212. In an option, the piston includes a recessed portion 210, and the stripped portion 206 is disposed within, and wrapped around the piston. The stripped portion 206 is electrically coupled with the piston, for example, by welding the stripped portion 206 to the piston. Other suitable methods for electrically coupling the anoidal coil 204 with the piston include, but are not limited to adhesive, or mechanical interconnect, friction fit, interference fit, etc. The break out portion 212 is optionally rotatable, but in another option is not allowed to move longitudinally when rotated. The rotation of the break out portion 212 further allows for the helix to rotate to be implanted within tissue, or disengaged from tissue.

The electrical interconnect, for example the spring such as a canted coil 181, is disposed about an outer periphery of the break out portion 212. The electrical interconnect electrically connects the anoidal coil 204 via the break out portion 212, with the anoidal stationary electrode while allowing the anoidal 204 coil to rotate, where the anoidal coil 204 and the cathodal coil 202 rotate and translate together. The spring provides redundant electrical contacts between the stationary component and the moveable break out portion 212 of the piston, while not interfering with the rotation or the movement of the movable break out portion 212.

Figure 6:
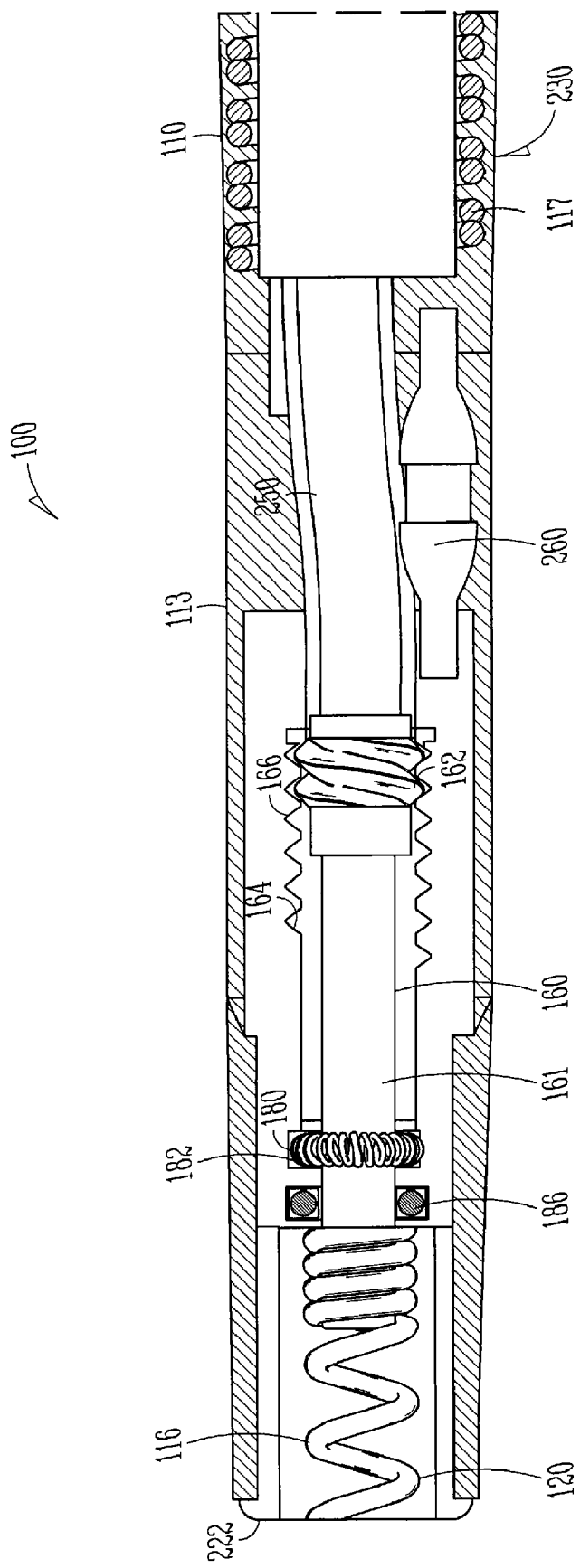
FIG. 6 is a cross-sectional view of a portion of a lead in a constructed in accordance with at least one embodiment.

FIG. 6 illustrates yet another example of the lead system 100 that includes an electrical connection between a rotating member to a stationary member. The example illustrated in FIG. 6 is a lead that includes features allowing for energy, such as MRI induced energy, to be shunted from the relatively small electrode, such as the fixation helix 120, to a relatively large electrode, such as a distal coil. The charge density is significantly reduced at the helix because a large percentage of the energy enters the body through distal coil 230, rather than the helix.

The lead system 100 includes an active fixation assembly including a fixation helix 120. The fixation helix 120 engages tissue at an interface 222, and serves as an electrode to the tissue. The fixation helix 120 is electrically coupled with an electrode base 160 that also serves as a piston for the fixation helix 120. The piston is further mechanically coupled with the fixation helix 120, and allows for the fixation helix 120 to be advanced moved relative to the lead body 113, for example by rotation and/or longitudinal movement.

The piston further optionally includes features that allow it to be moved longitudinally. For example, the piston includes a threaded portion 162 that engages with an internally threaded portion 164 of the housing 166. To move the piston in longitudinal movement, the piston is rotated and the threaded portions engage each other to advance the piston and the fixation helix. In an option, the piston is controlled at the proximal portion of the lead 110 (FIG. 1), for example by turning the pin.

The piston is electrically coupled with an electrical interconnect 180 that is included with the lead 110, for example at a distal tip of the lead body 113. Suitable examples of the electrical interconnect 180 include, but are not limited to, a spring, or a canted coil. The electrical interconnect 180 is electrically associated with the piston or the electrode base 160. For example, the electrical interconnect 180 has an inner portion that at least partially surrounds an outer periphery of the piston or electrode base, and optionally is in direct, electrical contact with the piston or the electrode base. In another option, a seal 186 is sealingly engaged with the outer periphery 161 of the piston or electrode base, which assists in preventing harmful fluids from entering the lead 110.

Referring again to the electrical interconnect 180, the electrical interconnect 180 is retained by a retention member, such as, but not limited to, a recess 182 or a protrusion coupled with or integral with a stationary electrode member 117, where the stationary electrode member 117 is stationary relative to the lead body 113. In an option, the recess is sized to electrically couple the electrical interconnect 180 with the stationary electrode member 117, for example, by direct contact between an electrically conductive electrical interconnect 180, for example formed of metal, and an electrically conductive stationary electrode member 117.

The electrical interconnect 180 provides a reliable electrical interconnection between the stationary electrode 117 and the non-stationary electrode 116, while allowing the non-stationary electrode to move relative to the stationary electrode 117, for example, as the piston is moved to advance the fixation helix 120. Suitable examples of the electrical interconnect 180 include any member that provides a substantially reliable electrical interconnection between the stationary electrode 117 and the non-stationary electrode that allows for the non-stationary electrode to move relative to the lead body 113 and/or the stationary electrode 117.

The lead system 100 further includes a sense coil 250, a distal coil 230, and a capacitor 260. The capacitor is electrically coupled with helix 120 and the distal coil. The capacitor selectively shunts energy from the helix 120 to the distal coil 230 as a function of frequency. The value of the capacitor is chosen, in an option, such that it behaved as an open circuit at frequencies associated with pacing and sensing, for example at frequencies less than, or substantially less than 1 MHz. The capacitor would behave as a short circuit at frequencies associated with MRI or other interference sources, such as at frequencies greater, or significantly greater than 1 MHz. During normal pacing and sensing, the capacitor is an open circuit. During high frequency, such as amounts experienced in magnetic resonance imaging, the capacitor closes the circuit to reduce charge density at the helix 120. The energy is shunted from the helix 120 to the distal coil 230 via the capacitor.

A method of using the lead is further described herein. The method includes moving an active fixation assembly of an implantable lead system relative to an elongate, flexible lead body, where the elongate, flexible lead body extends from a proximal portion to a distal portion and the active fixation assembly is within the elongate flexible lead body. The lead system is optionally coupled with an energy source, such as, but not limited to, a pulse generator. The active fixation assembly is moved longitudinally, for example by rotation, to implant the active fixation member in tissue. The method further includes electrically interconnecting the active fixation assembly with a stationary electrode member while the active fixation assembly is moved, for example by rotation. The electrically interconnection includes placing a canted coil against an outer periphery of the active fixation assembly, or placing the coil against an inner periphery of the stationary electrode member, or using redundant electrical contacts. Further options for the method include diverting energy from the active fixation assembly to the stationary electrode with a shunt, such as a capacitor. This is done during episodes of high frequency, such as during an MRI.

It is to be understood that the above description is intended to be illustrative, and not restrictive. Although the use of the implantable device has been described for use as a lead in, for example, a cardiac stimulation system, the implantable device could as well be applied to other types of body stimulating systems. Many other embodiments will be apparent to those of skill in the art upon reviewing the above description. The scope should, therefore, be determined with reference to the appended claims, along with the full scope of equivalents to which such claims are entitled.

What is claimed is:

1. A lead system comprising:
    an elongate lead body extending from a proximal end portion to a distal end portion;
    an active fixation mechanism movable longitudinally relative to the elongate lead body;
    a stationary electrode member at the distal end portion;
    a non-stationary electrode member at the distal end portion, the non-stationary electrode member movable longitudinally relative to the elongate lead body between a retracted position and an extended position;
    at least one annular electrical interconnect in the distal end portion including an outer diameter electrically connected to the stationary electrode member and an inner diameter electrically connected to the non-stationary electrode member, wherein the non-stationary electrode member moves relative to and remains in mechanical and electrical contact with the inner diameter of the at least one annular electrical interconnect when the non-stationary electrode member is moved longitudinally between the retracted position and the extended position; and
    a capacitor electrically connected to the non-stationary electrode member and stationary electrode member, wherein the capacitor is configured such that, at frequencies associated with magnetic resonance imaging (MRI), the capacitor operates as a short circuit between the non-stationary electrode member and stationary electrode member and, at frequencies associated with pacing and sensing, the capacitor operates as an open circuit between the non-stationary electrode member and stationary electrode member.

2. The lead system as recited in claim 1, wherein the electrical interconnect has redundant electrical contacts integral therewith.

3. The lead system as recited in claim 1, wherein the electrical interconnect includes a canted coil.

4. The lead system as recited in claim 1, wherein the stationary electrode member is a shocking coil.

5. The lead system as recited in claim 1, wherein the non-stationary electrode member is rotatable relative to a longitudinal axis of the elongate lead body.

6. The lead system as recited in claim 1, wherein the at least one electrical interconnect includes redundant electrical contacts.

7. The lead system as recited in claim 1, further comprising at least one conductor, wherein the at least one conductor includes a first conductor and a second conductor, and the first and second conductors are co-radial.

8. The lead system as recited in claim 7, further comprising a terminal ring, an anode ring, and an anodal coil, and the at least one electrical interconnect interconnects the terminal ring and the anode ring with the anodal coil.

9. An apparatus comprising:
a lead system including an elongate lead body extending from a proximal end portion to a distal end portion;
at least one conductor disposed within at least a portion of the lead body;
a stationary electrode member at the distal end portion;
an active fixation assembly including a non-stationary electrode member at the distal end portion, wherein the active fixation assembly is movable longitudinally relative to the elongate lead body to move the non-stationary electrode member between a retracted position and an extended position; and
at least one annular electrical interconnect at the distal end portion including an inner diameter and an outer diameter, the inner diameter electrically connected to the non-stationary electrode member and the outer diameter electrically connected to the stationary electrode member, wherein the non-stationary electrode member moves relative to and remains in mechanical and electrical contact with the inner diameter of the at least one annular electrical interconnect when the non-stationary electrode member is moved longitudinally between the retracted position and the extended position; and
a capacitor electrically connected to the non-stationary electrode member and stationary electrode member, wherein the capacitor is configured such that, at frequencies associated with magnetic resonance imaging (MRI), the capacitor operates as a short circuit between the non-stationary electrode member and stationary electrode member and, at frequencies associated with pacing and sensing, the capacitor operates as an open circuit between the non-stationary electrode member and stationary electrode member.

10. The apparatus as recited in claim 9, wherein the means for interconnecting is a canted coil.

11. The apparatus as recited in claim 9, wherein the at least one conductor includes a first conductor and a second conductor, and the first and second conductors are co-radial.

12. The apparatus as recited in claim 11, further comprising a terminal ring, an anode ring, and an anodal coil.

13. The apparatus as recited in claim 12, wherein means for electrically interconnecting the non-stationary electrode member with the stationary electrode member electrically interconnects the terminal ring and the anode ring with the anodal coil.

14. A method comprising:
moving an active fixation assembly of an implantable lead system longitudinally relative to an elongate, flexible lead body, the elongate, flexible lead body extending from a proximal portion to a distal portion and the active fixation assembly is within the elongate flexible lead body at the distal end portion;
electrically interconnecting the active fixation assembly with a stationary electrode member with an annular electrical interconnect at the distal end portion such that the active fixation assembly moves relative to and remains in mechanical and electrical contact with an inner diameter of the annular electrical interconnect while the active fixation assembly is moved longitudinally between a retracted position and an extended position; and
connecting a capacitor between the active fixation assembly the stationary electrode member, wherein the capacitor is configured such that, at frequencies associated with magnetic resonance imaging (MRI), the capacitor operates divert energy from the active fixation assembly to the stationary electrode member and, at frequencies associate with pacing and sensing, the capacitor operates as an open circuit.

15. The method as recited in claim 14, wherein moving the active fixation assembly includes rotating the active fixation assembly.

16. The method as recited in claim 14, wherein electrically interconnecting the active fixation assembly includes placing a canted coil against an outer periphery of the active fixation assembly.

17. The method as recited in claim 14, wherein electrically interconnecting the active fixation assembly includes redundantly contacting the active fixation assembly and the stationary electrode member.

18. The method as recited in claim 14, wherein electrically interconnecting the active fixation assembly includes placing a canted coil against an inner periphery of the stationary electrode member.

19. The method as recited in claim 16, further comprising electrically coupling the lead system with an energy source.

* * * * *